United States Patent
Narimatsu et al.

(10) Patent No.: US 7,097,621 B2
(45) Date of Patent: Aug. 29, 2006

(54) FILTER FOR USE WITH PULSE-WAVE SENSOR AND PULSE WAVE ANALYZING APPARATUS

(75) Inventors: Kiyoyuki Narimatsu, Komaki (JP); Akira Tampo, Komaki (JP); Takashi Honda, Komaki (JP)

(73) Assignee: Colin Medical Technology Corporation, Komaki (JP)

( * ) Notice: Subject to any disclaimer, the term of this patent is extended or adjusted under 35 U.S.C. 154(b) by 361 days.

(21) Appl. No.: 10/760,582

(22) Filed: Jan. 21, 2004

(65) Prior Publication Data
US 2004/0171944 A1 Sep. 2, 2004

(30) Foreign Application Priority Data
Jan. 24, 2003 (JP) .............................. 2003-015813

(51) Int. Cl.
*A61B 5/00* (2006.01)
(52) U.S. Cl. .................. 600/500; 600/485; 600/500
(58) Field of Classification Search .................. None
See application file for complete search history.

(56) References Cited

U.S. PATENT DOCUMENTS
6,379,309 B1 * 4/2002 Ogura et al. ............... 600/490

FOREIGN PATENT DOCUMENTS
JP A 2001-145606 5/2001

* cited by examiner

*Primary Examiner*—Robert L. Nasser
*Assistant Examiner*—Karen E. Toth
(74) *Attorney, Agent, or Firm*—Oliff & Berridge, PLC

(57) ABSTRACT

A pulse wave analyzing apparatus including a cuff 12 for detecting a pulse wave from a living subject, a pressure sensor 16 for converting the pulse wave detected by the cuff 12, into an electric signal, i.e., a pulse wave signal SM, a plurality of band-pass filters 62 (BPF(1), BPF(2), . . . , BPF(n)) that have respective low-side cuff-off frequency bands differing from each other and each receive the pulse wave signal SM, a provisional rising point determining device 64 for determining respective times PS of respective provisional rising points of respective pulse waves represented by respective secondary pulse wave signals SM2 that have passed through the band-pass filters 62, and a proper rising point determining device 66 for comparing the respective times PS of respective provisional rising points with each other and thereby determining a time AS of a proper rising point based on the respective times PS of respective provisional rising points.

5 Claims, 8 Drawing Sheets

FILTER FOR USE WITH PULSE-WAVE SENSOR AND PULSE WAVE ANALYZING APPARATUS

BACKGROUND OF THE INVENTION

1. Field of the Invention

The present invention relate to a filter for use with a pulse wave sensor in determining a rising point of a pulse wave, and a pulse wave analyzing apparatus that determines a rising point of a pulse wave by analyzing the shape or form of the pulse wave.

2. Related Art Statement

A rising point of a pulse wave is identified or determined, for example, when a pulse wave propagation velocity at which the pulse wave propagates between two body portions of a living subject is measured, or when a pulse rate of the subject is measured. There is known a pulse wave sensor that is worn on a body portion of a living subject to detect a pulse wave from the body portion, and outputs a pulse wave signal representing the detected pulse wave. However, the pulse wave signal contains, in addition to components representing the pulse wave, low-frequency noise such as swell like DC component, or high-frequency noise such as artifact noise or background noise. Hence, a pulse wave filter is used to remove the noise and obtain a filtered pulse wave signal representing a desired pulse wave.

When the rising point of pulse wave is utilized, such a pulse wave filter is employed which has a specific frequency band covering frequencies of a rising portion of the pulse wave and allows the rising portion to pass therethrough. For example, a pulse wave filter disclosed by Japanese Patent Publication No. 2001-145606 has a specific frequency band of from 1 Hz to 30 Hz.

However, even in the case where the pulse wave filter that allows the rising portion of pulse wave to pass therethrough is employed and the pulse wave signal filtered by the filter is used to determine the rising point of pulse wave, the rising portion of the pulse wave represented by the filtered signal may not be so sharp as to be able to determine sufficiently accurately a time of detection or occurrence of the rising point.

SUMMARY OF THE INVENTION

It is therefore an object of the present invention to provide a filter for use with a pulse wave sensor in determining accurately a rising point of a pulse wave, and a pulse wave analyzing apparatus that can accurately determine the rising point of pulse wave.

The Inventors have carried out extensive studies to achieve the above-indicated object, and have found the following facts: A pulse wave, that is, a composite wave of an incident wave traveling from subject's heart to his or her peripheral-side portion and a reflected wave produced when the incident wave is reflected by a bifurcated portion of the peripheral side, has such features that the incident wave shows a sharp rising portion since it is produced when blood is ejected from the heart whereas the reflected wave shows a gentle rising portion since its high-frequency component is attenuated during propagation through artery and its low-frequency component is relatively enhanced. Therefore, a gentle rising portion of a pulse wave is caused by its reflected wave component and, if the reflected wave component is removed from the pulse wave, its incident wave component is relatively enhanced and the rising portion of the pulse wave is sharpened, so that the accuracy of determination of the rising point is improved. The present invention has been developed on this finding.

According to a first aspect of the present invention, there is provided a filter for use with a pulse wave sensor which is adapted to be worn on a body portion of a living subject to detect a pulse wave from the body portion, and outputs a signal representing the detected pulse wave, wherein the filter cuts off a reflected wave component of the signal that has frequencies falling within a low frequency band, and allows a rising portion of an incident wave component of the signal that has frequencies falling within a high frequency band, to pass therethrough.

According to the first aspect of the present invention, the pulse wave represented by the signal filtered by the present filter has such features that the reflected wave component as the low-frequency component has been removed and the incident wave component has been enhanced. Therefore, the pulse wave represented by the filtered signal shows a sharp rising portion. Thus, the time of rising point of the pulse wave can be accurately determined based on the signal filtered by the filter.

An average frequency of a reflected wave component of a pulse wave be experimentally determined, in advance, and the filter according to the first aspect of the present invention can be adapted to have a low-side cut-off frequency band whose upper limit is determined based on the average frequency. In this case, the accuracy of determination of rising point is improved. However, the frequency of reflected wave component differs among individual patients or among different body portions of each patient. Hence, a pulse wave analyzing apparatus according to a second aspect of the present invention employs a plurality of filters having respective low-side cut-off frequency bands differing from each other, determines respective times of respective rising points of respective pulse waves represented by the respective signals filtered by the filters, and determines a time of a single rising point by comparing the thus determined respective times of respective rising points with each other.

According to a second aspect of the present invention, there is provided a pulse wave analyzing apparatus comprising a pulse wave sensor which is adapted to be worn on a body portion of a living subject to detect a pulse wave from the body portion, and outputs a pulse wave signal representing the detected pulse wave; a plurality of filters for use with the pulse wave sensor, the plurality of filters having respective low-side cut-off frequency bands differing from each other, and each receiving the pulse wave signal outputted by the pulse wave sensor; a provisional rising point determining means for determining a time of detection of a provisional rising point of each of respective pulse waves represented by respective signals that have passed through the filters; and a proper rising point determining means for comparing the respective times of detection of the respective provisional rising points, each determined by the provisional rising point determining means, with each other, and thereby determining a time of detection of a proper rising point based on the respective times of detection of the respective provisional rising points.

According to the second aspect of the present invention, the provisional rising point determining means determines the respective times of respective provisional rising points of respective pulse waves represented by the respective signals that have passed through the filters having the respective different low-side cut-off frequency bands, and the proper rising point determining means compares the respective times of respective provisional rising points with each other and thereby determines the time of proper rising point based on the respective times of respective provisional rising points. Therefore, even if respective rising portions of respective reflected wave components and/or respective incident wave components of respective pulse waves detected from different patients or different body portions of each individual patient may have different frequencies or different frequency bands, the present pulse-wave analyzing apparatus can accurately determine a time of a rising point of a pulse wave detected from each of the patients or each of the body portions of each individual patient.

According to a first feature of the second aspect of the present invention, the proper rising point determining means determines, when at least two times of the, respective times of detection of the respective provisional rising points are substantially equal to each other, the at least two times substantially equal to each other, as the time of detection of the proper rising point. The respective pulse waves represented by the respective signals filtered by the filters having the respective different low-side cut-off frequency bands, show respective sharp rising portions similar to each other, if respective upper limits of the respective low-side cut-off frequency bands of the filters are higher than the frequencies of the respective reflected wave components of the respective pulse waves. Therefore, the respective times of respective rising points of those sharp rising portions are substantially equal to each other. Thus, the present apparatus can accurate determine a time of a rising point of a pulse wave.

According to a second feature of the second aspect of the present invention, the proper rising point determining means determines, when the respective times of detection of the respective provisional rising points of the respective pulse waves represented by the respective signals that have passed through the filters decrease as respective upper limits of the respective low-side cut-off frequency bands of the corresponding filters increase, a shortest one of the respective times of detection of the respective provisional rising points, as the time of detection of the proper rising point. In this case, it is thought that the reflected wave components as the respective low-frequency components have not been removed from the respective pulse waves and the respective rising portions have been delayed by those reflected wave components. Therefore, the proper rising point determining means determines the shortest one of the respective times of detection of the respective provisional rising points, as the time of detection of the proper rising point.

The pulse wave sensor may be a cuff that is wound around a body portion of a subject to press the body portion; a photoelectric pulse wave detecting probe for use in measurement of blood oxygen saturation; a pressure pulse wave sensor that is pressed via skin to an artery such as a radial artery to detect a pressure pulse wave from the artery; an impedance pulse wave sensor that detects, through electrodes, an impedance pulse wave from, e.g., an arm or a finger; or a photoelectric pulse wave sensor that is worn on, e.g., a tip of a finger to detect a pulsation. Alternatively, the pulse wave sensor may be an invasive-type pulse wave sensor that includes a catheter directly inserted in an artery and a pressure transducer connected to the catheter to detect a pulse wave from the artery.

According to a third feature of the second aspect of the present invention, the pulse-wave sensor comprising an inflatable cuff adapted to be worn on the body portion of the subject, and wherein the proper rising point determining means determines, when the respective times of detection of the respective provisional rising points of the respective pulse waves represented by the respective signals that have passed through the filters increase as respective upper limits of the respective low-side cut-off frequency bands of the corresponding filters increase, a shortest one of the respective times of detection of the respective provisional rising points, as the time of detection of the proper rising point. In the case where the pulse wave sensor is provided by the cuff and a pulse wave as a pressure oscillation transmitted from an artery to the cuff propagates from the cuff to a pressure sensor via a tube, the oscillation of the pulse wave is attenuated, and the phase of the same is delayed, during propagation of the pulse wave through the tube. The amounts of delay of phases of high-frequency components of the pulse wave are larger than those of low-frequency components of the same. Therefore, the amounts of delay of phases of high-frequency components of the pulse wave are so large as to influence the determination of time of rising point of the pulse wave, the respective times of detection of the respective provisional rising points of the respective pulse waves represented by the respective signals filtered by the filters increase as the respective upper limits of the respective low-side cut-off frequency bands of the corresponding filters increase.

BRIEF DESCRIPTION OF THE DRAWINGS

The above and optional objects, features, and advantages of the present invention will be better understood by reading the following detailed description of preferred embodiments of the invention when considered in conjunction with the drawings, in which.

DETAILED DESCRIPTION OF PREFERRED EMBODIMENTS

Figure 1:
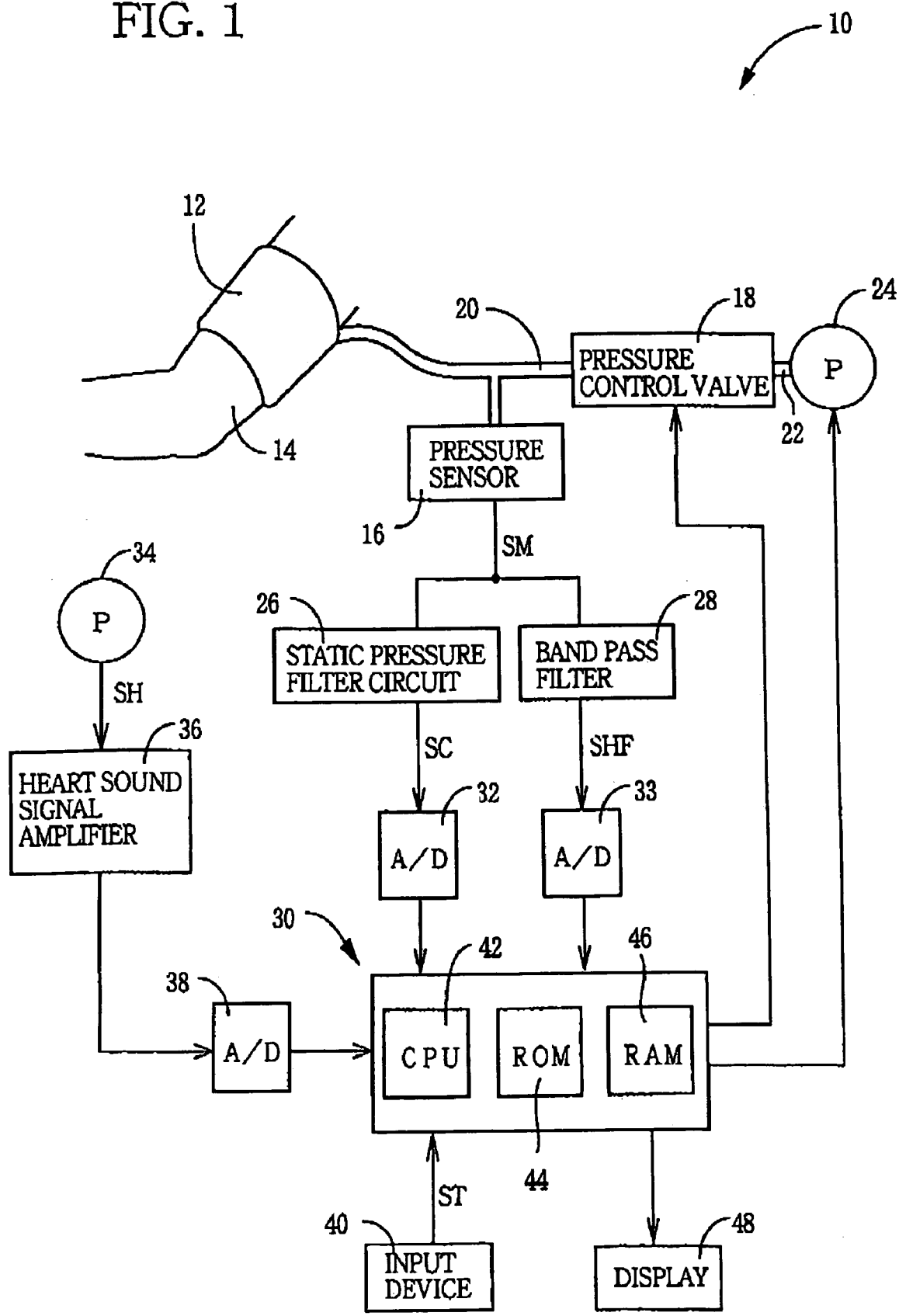
FIG. 1 is a diagrammatic view for explaining a construction of a pulse-wave propagation velocity measuring apparatus including a pulse-wave filter to which the present invention is applied.

Hereinafter, there will be described a preferred embodiment of the present invention in detail by reference to the drawings. FIG. 1 is a diagrammatic view for explaining a construction of a pulse-wave propagation velocity measuring apparatus 10 including a pulse wave filter to which the present invention is applied.

In FIG. 1, the pulse-wave propagation velocity measuring apparatus, 10 includes a cuff 12 which functions as a pulse wave sensor and includes a belt-like cloth bag and a rubber bag accommodated in the cloth bag, and which is adapted to be worn on a brachium 14 of a living subject. The cuff 12 is connected via a piping 20 to a pressure sensor 16 and a pressure control valve 18. The piping 20 is formed of rubber or a flexible resin. The pressure control valve 18 is connected via a piping 22 to an air pump 24. The pressure control valve 18 adjusts a pressure of a pressurized air supplied from the air pump 24, and supplies the pressure-adjusted air to the cuff 12, or discharges the pressurized air from the cuff 12, so as to control an air pressure in the cuff 12.

In a state in which the cuff 12 is inflated around the brachium 14, a pulse wave produced from an artery not shown, of the brachium 14 is transmitted to the cuff 12, so that a pressure oscillation corresponding to the pulse wave is produced in the cuff 12. Hereinafter, this pressure oscillation will be referred to as the cuff pulse wave. The cuff pulse wave is transmitted via the piping 20 to the pressure sensor 16. Thus, the cuff 12 outputs, as an output signal thereof, the cuff pulse wave as the pressure oscillation.

The pressure sensor 16 converts the cuff pulse wave transmitted as the pressure oscillation, into an electric signal i.e., a pulse wave signal SM, and supplies the pulse wave signal SM to each of a static-pressure filter circuit 26, and a band-pass filter 28 functioning as the pulse wave filter. The static-pressure filter circuit 26 includes a low-pass filter which extracts, from the pulse wave signal SM, a cuff pressure signal SC representing a static component of the signal SM, i.e., a pressing pressure of the cuff 12 (hereinafter, referred to as the cuff pressure PC). The filter circuit 26 supplies the cuff pressure signal SC to an electronic control device 30 via an A/D (analog-to-digital) converter 32.

The band-pass filter 28 has a specific frequency band, and allows only signals or signal components having frequencies falling within the specific frequency band, to pass therethrough. The specific frequency band of the band-pass filter 28 is higher than a low frequency band within which frequencies of a reflected wave component of the cuff pulse wave detected by the cuff 12 fall, contains a high frequency band within which frequencies of a rising portion of an incident wave component of the cuff pulse wave fall, and is lower than a higher frequency band within which frequencies of high-frequency noise fall. Since, in the present embodiment, the cuff 12 is worn on the brachium 14 and accordingly the cuff 12 detects a brachial pulse wave as the cuff pulse wave, the band-pass filter 28 has, e.g., a specific frequency band of from 20 Hz to 40 Hz. Thus, when the pulse wave signal SM passes through the band-pass filter 28, the reflected wave component of the brachial pulse is removed from the signal SM and accordingly the rising portion of the incident wave component of the same is relatively enhanced. Hereinafter, this pulse wave signal SM will be referred to as the "high-frequency pulse wave signal SHF", where appropriate. The high-frequency pulse wave signal SHF is supplied to the electronic control device 30 via an A/D converter 83.

A heart-sound microphone 34 is attached, with, e.g., an adhesive tape not shown, to a chest of the subject. The heart-sound microphone 34 incorporates a piezoelectric element, not shown, which converts heart sounds produced from the heart of the subject, into an electric signal i.e., a heart-sound signal SH representing a waveform of the heart sounds. A heart-sound-signal amplifier 36 incorporates four sorts of filters, not shown, which cooperate with each other to attenuate a low-pitch component of the heart sounds that has a great energy, so as to allow clear recording of a high-pitch component of the heart sounds. The heart-sound signal SH supplied from the heart-sound microphone 34 is amplified and filtered by the heart-sound-signal amplifier 36, and then is supplied to the electronic control device 30 via an A/D converter 38.

An input device 40 includes a keyboard, not shown, which is operable for inputting numerals representing a stature T of the subject, and supplies a stature signal ST representing the subject's stature T inputted through the keyboard, to the electronic control device 30.

The electronic control device 30 is provided by a so-called microcomputer including a CPU (central processing unit) 42, a ROM (read only memory) 44, a RAM (random access memory) 46, and an I/O (input-and-output) port, not shown. The CPU 42 processes signals according to control programs pre-stored in the ROM 44, while utilizing a temporary-storage function of the RAM 46. The CPU 42 outputs, from the I/O port, drive signals to the air pump 24 and the pressure control valve 26, so as to control the cuff pressure PC. In addition, the CPU 42 provides control functions shown in FIG. 2, and accordingly identifies a rising point of a heartbeat-synchronous pulse of the cuff pulse wave detected by the cuff 12, calculates a pulse-wave propagation velocity PWV based on the identified rising point, and operates a display device 48, such as a CRT (cathode ray tube) or an LCD (liquid crystal display), to display the thus calculated velocity PWV.

Figure 2:
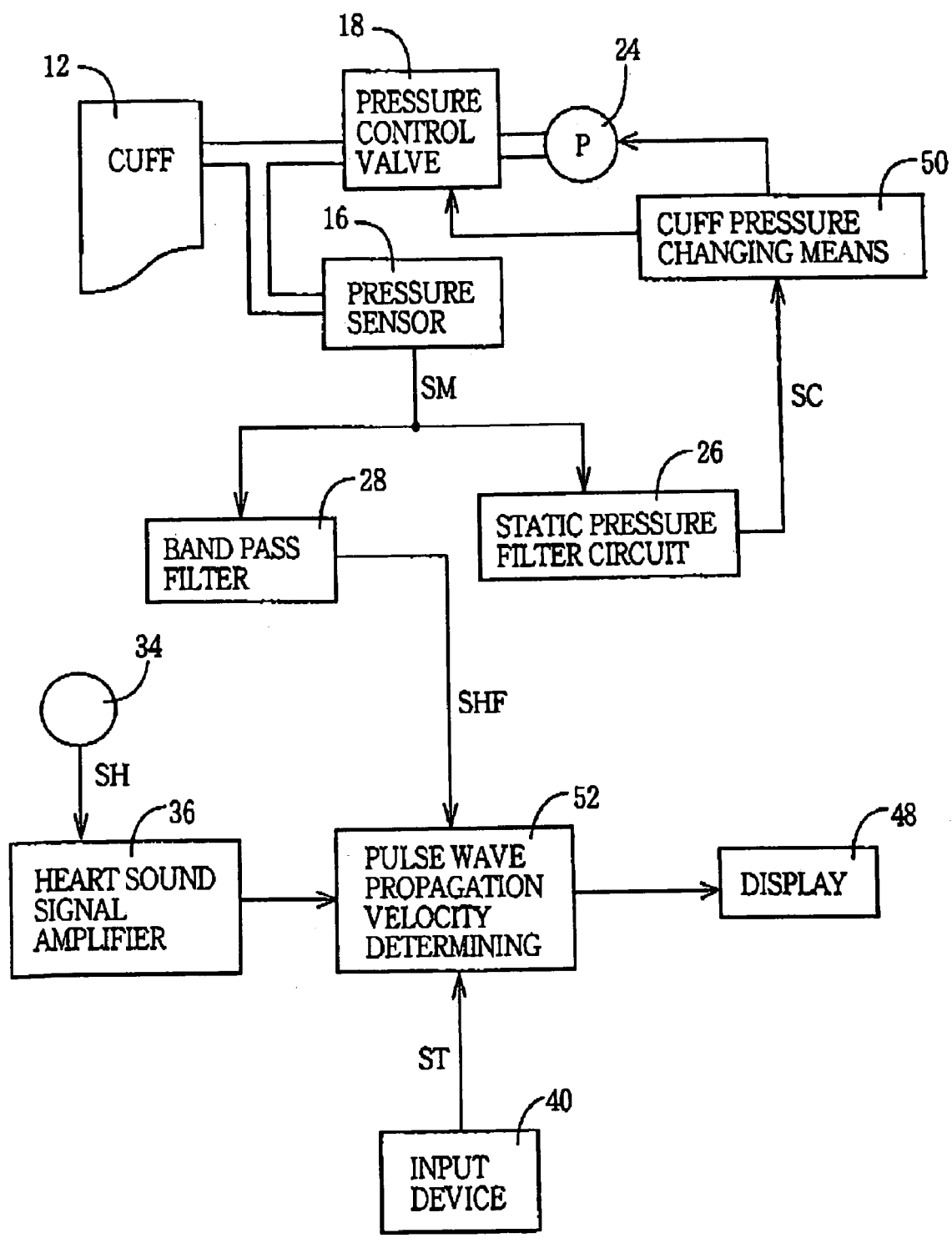
FIG. 2 is a diagrammatic view for explaining essential control functions of an electronic control device of the apparatus shown in FIG. 1.

FIG. 2 is a diagrammatic view for explaining essential control functions of the electronic control device 30 of the pulse-wave propagation velocity measuring apparatus 10.

A cuff-pressure changing device or means 50 reads the cuff pressure PC represented by the cuff pressure signal SC supplied from the static-pressure filter circuit 26, and controls the pressure control valve 18 and the air pump 24, so as to change and maintain the cuff pressure PC to and at a prescribed pulse-wave detection pressure value. The pulse-wave detection pressure value is so prescribed as to be lower than a diastolic blood pressure of the brachium 14 around which the cuff 12 is wound and assure that a sufficiently large pressure oscillation is produced in the cuff 12. In the present embodiment, the pulse-wave detection pressure value is 50 mmHg.

A pulse-wave propagation velocity determining device or means 52 first determines a time of detection of a start point of a heart sound I of the heart sound waveform represented by the heart sound signal SH supplied from the heart-sound microphone 34, in a state in which the cuff pressure changing means 50 maintains the cuff pressure PC at the pulse-wave detection pressure value, and additionally determines a time of detection of a rising point of a heartbeat-synchronous pulse of the cuff pulse wave represented by the high-frequency pulse wave signal SHF supplied from the band pass filter 28, in the same state. In the present embodiment, a minimum-point identifying method is employed to identify a rising point of a heartbeat-synchronous pulse of a cuff pulse wave. In the minimum-point identifying method, a minimum point of a heartbeat-synchronous pulse of a cuff pulse wave is identified as a rising point of the pulse. Subsequently, the determining means 52 determines a time difference (sec) between the time of start point of the heart sound I and the time of rising point of the pulse wave, as a pulse-wave propagation time DT in which a pulse wave (i.e., the cuff pulse wave) propagates from the subject's heart to a portion of the subject (i.e., the brachium 14) where the cuff 12 is worn. Then, the determining means 52 substitutes the subject's stature T represented by the stature signal ST supplied from the input device 40, with the following Expression 1 representing a relationship between stature T and propagation distance L, pre-stored in the ROM 44:

$$L=aT+b \quad \text{(Expression 1)}$$

where a and b are experimentally determined constants.

Thus, the determining means 52 determines the propagation distance L between the heart and the brachium 14. In addition, the determining means 52 substitutes the propagation distance L and the pulse-wave propagation time DT with the following Expression 2, so as to calculate a pulse-wave propagation velocity PWV (cm/sec):

$$PWV=L/DT \quad \text{(Expression 2)}$$

Finally, the determining means 52 operates the display device 48 to display the thus calculated pulse-wave propagation velocity PWV.

In the present pulse-wave propagation velocity measuring apparatus 10, the high-frequency pulse wave signal SHF that has passed through the band-pass filter 28 represents a sharp and clear rising portion of the cuff pulse wave, because the reflected wave component thereof as the low-frequency component has been removed and the rising portion of the incident wave component thereof has been enhanced. Therefore, the time of rising point identified based on the high-frequency pulse wave SHF as the output of the band-pass filter 28 enjoys improved accuracy, and accordingly the pulse-wave propagation velocity PWV calculated based on the thus identified rising point also enjoys improved accuracy.

Next, there will be described a second embodiment of the present invention that also relates to a pulse-wave propagation velocity measuring apparatus. The same reference numerals as used in the first embodiment shown in FIGS. 1 and 2 are used to designate the corresponding elements or parts of the second embodiment, and the description thereof is omitted.

Figure 3:
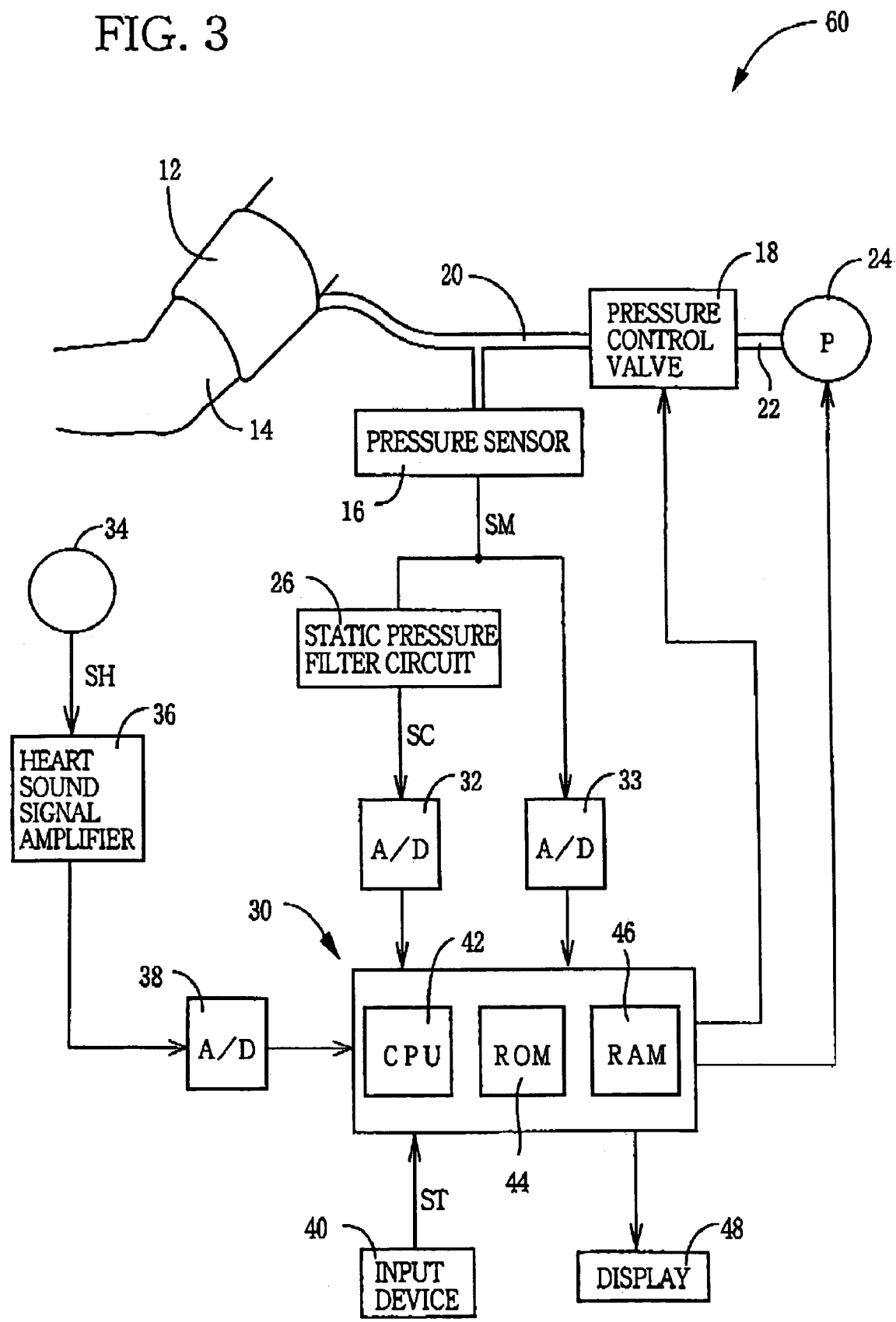
FIG. 3 is a diagrammatic view for explaining a construction of another pulse-wave propagation velocity measuring apparatus functioning as a pulse-wave analyzing apparatus to which the present invention is applied.

FIG. 3 is a diagrammatic view for explaining a construction of a pulse-wave propagation velocity measuring apparatus 60, as the second embodiment of the present invention, that functions as a pulse wave analyzing apparatus. The second apparatus 60 differs from the first apparatus 10 only in that the second apparatus 60 does not employ the band-pass filter 28 employed by the first apparatus 10 and accordingly the pulse wave signal SM is directly supplied to the electronic control device 30, and in that control functions of the control device 30 of the second apparatus 60 differ from those of the control device 30 of the first apparatus 10.

Figure 4:
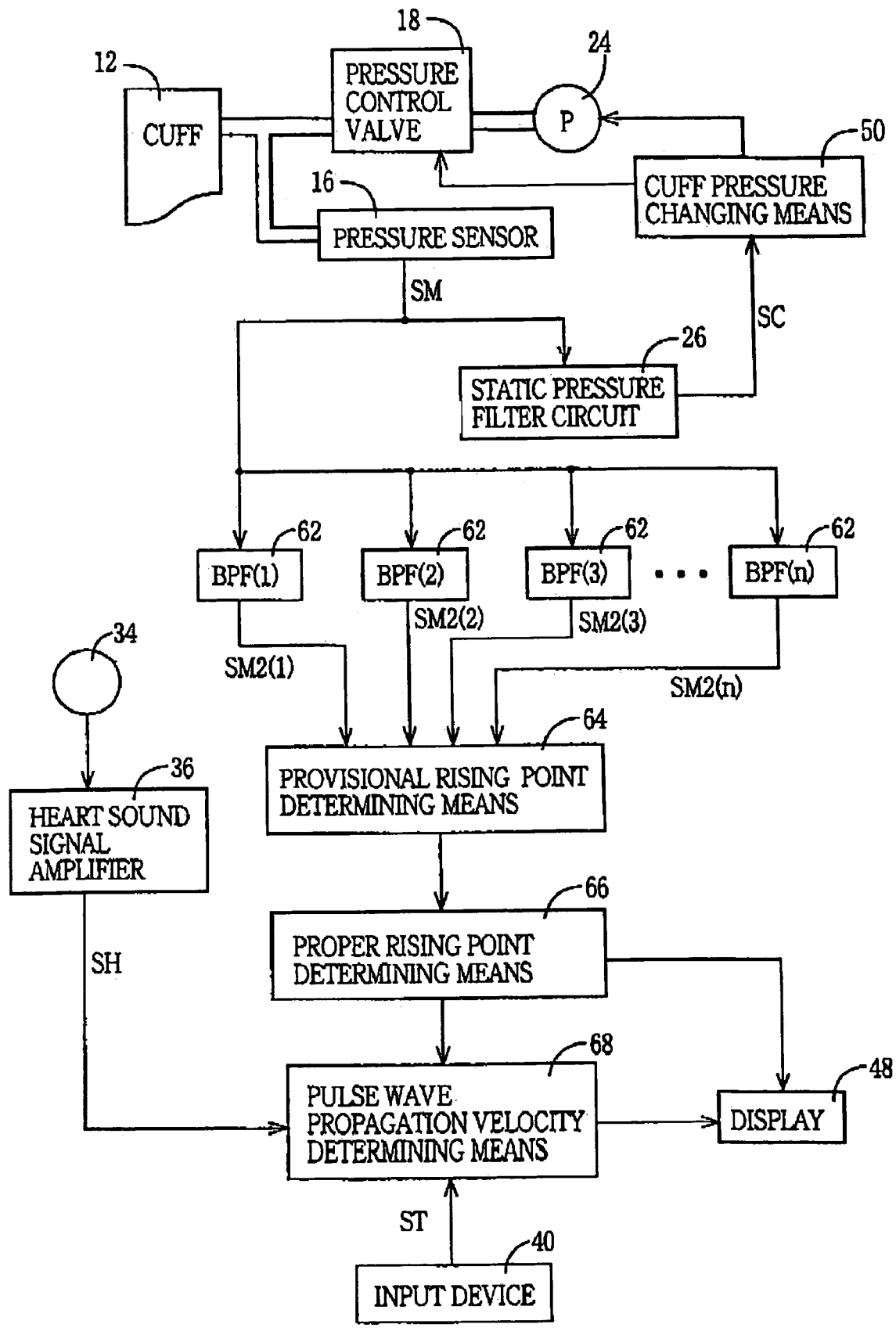
FIG. 4 is a diagrammatic view for explaining essential control functions of an electronic control device of the apparatus shown in FIG. 3.

FIG. 4 is a diagrammatic view for explaining essential control functions of the electronic control device 30 of the pulse-wave propagation velocity measuring apparatus 60 shown in FIG. 3.

A plurality of band-pass filters 62 (BPF(1), BPF(2), BPF(3), . . . , BPF(n); n is a natural number indicating a number assigned to each filter) that cooperate with each other to function as a pulse wave filter, are provided by a plurality of digital filters, respectively, each of which has a specific frequency band and has a function of processing a digital signal and extracting, from the digital signal a signal component having frequencies falling within the specific frequency band. However, the plurality of band-pass filters 62 have different specific frequency bands. The band-pass filters 62 extract, from the pulse wave signal SM supplied from the pressure sensor 16, respective oscillatory components corresponding to the respective specific frequency bands thereof and output respective secondary pulse wave signals SM2(1), SM2(2), SM2(3), . . . , SM2(n) representing the respective extracted oscillatory components.

Figure 5:
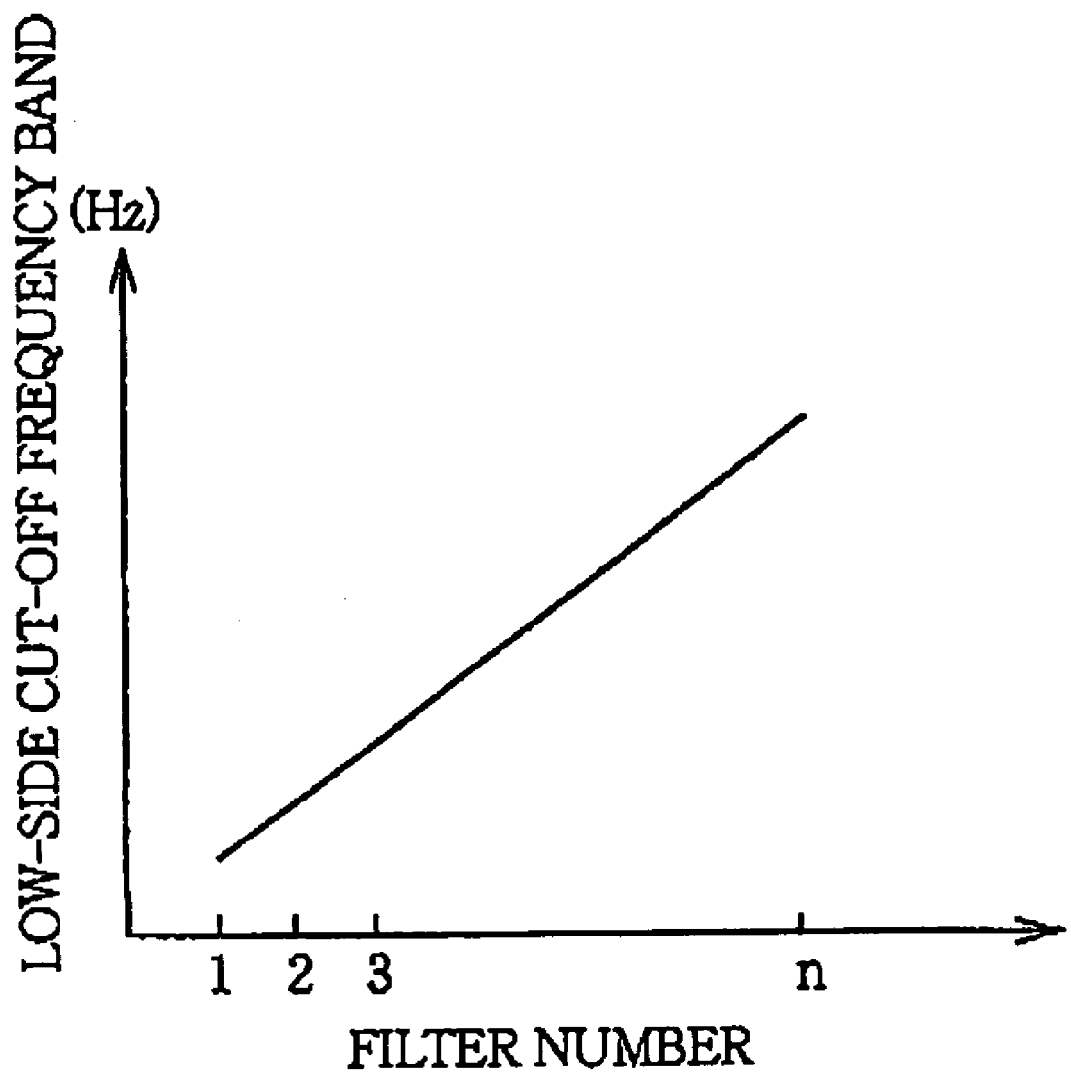
FIG. 5 is a view for explaining respective low-side cut-off frequency bands of a plurality of band-pass filters BPF shown in FIG. 4.

The respective specific frequency bands of the band-pass filters 62 are prescribed such that respective upper limits of respective low-side cut-off frequency bands lower than the respective specific frequency bands of the filers 62 gradually increase as the numbers (n) assigned to the filters 62 increase, as shown in FIG. 5. In addition, the highest one of the respective upper limits of respective low-side cut-off frequency bands of the band-pass filters 62, e.g., the upper limit of low-side cutoff frequency band of the filter BPF(n) shown in FIG. 5 is so prescribed as to be sufficiently lower than the frequencies of rising portion of the incident wave component of the pulse wave detected from the observed portion (e.g., the brachium 14) of the subject. In the case where the observed portion is the brachium 14, the upper limit of low-side cut-off frequency band of the filter BPF(n) is prescribed at 20 Hz, 25 Hz, or 30 Hz.

Meanwhile, so long as respective lower limits of respective high-side cut-off frequency bands higher than the respective specific frequency bands of the band-pass filters 62 are higher than the frequencies of rising portion of the incident wave component of the pulse wave detected from the observed portion, and are lower than the frequencies of high-frequency noise such as environmental noise, the respective lower limits of the respective high-side cut-off frequency bands may differ from each other or may be equal to each other.

A provisional rising point identifying device or means 64 determines respective times PS(1), PS2(2), . . . PS2(n) of respective provisional rising points of respective heartbeat-synchronous pulses of the respective cuff pulse waves represented by the secondary pulse wave signals SM2(1) SM2(2), . . . , SM2(n) supplied from the band-pass filters 62. In this embodiment, too, the minimum-point detecting method is employed to determine the respective times of respective provisional rising points PS(1), PS2(2), PS2(3), . . . , PS2(n).

A proper rising point identifying device or means 64 compares the respective times PS(i), PS2(2), . . . , PS2(n) of respective provisional rising points, determined by the provisional rising point identifying means 64, with each other, and selects, as a time AS of a proper rising point, an appropriate one of the respective times PS(1), PS2(2), PS2(n). For example, in a first case where the respective times PS of respective provisional rising points decrease as the respective upper limits of respective low-side cut-off frequency bands of the band-pass filters 62 increase, and become substantially constant in a high frequency range, as indicated at curve L1 in FIG. 6, the determining means 66 selects the substantially constant times PS of provisional rising points, as the time AS of proper rising point, because the substantially constant times PS of provisional rising points are thought to have been determined based on the respective sharp rising portions of the pulse waves from which the respective reflected wave components have been removed In a second case where the respective times PS of respective provisional rising points monotonously decrease as the respective upper limits of respective low-side cut-off frequency bands of the band-pass filters 62 increase, as indicated at curve L2 in FIG. 6, the proper rising point determining means 66 selects, as the time AS of proper rising point, the shortest one of the respective times PS of respective provisional rising points, e.g., the time PS(n) shown in FIG. 6, because the respective upper limits of respective low-side cut-off frequency bands are thought to be not high enough to cut off sufficiently the respective reflected wave components of the pulse waves and accordingly the respective times PS of respective provisional rising points decrease as the respective reflected wave components decrease. Here, the reason why time of rising point decreases as reflected wave component decreases by removal. FIG. 7 shows a graph showing respective rising portions of an incident wave component, wi, and a reflected wave component, wr. As shown in the figure, the incident wave component wi has a sharp rising portion with a rising point, a; and the refected wave component wr has a moderate rising portion with a rising point b. Therefore, an observed pulse wave, not shown, as a composite pulse wave of the incident and reflected wave components wi, wr has a rising point that is later or longer than the rising point a. Therefore, time of rising point decreases as influence of reflected wave component decreases.

Figure 6:
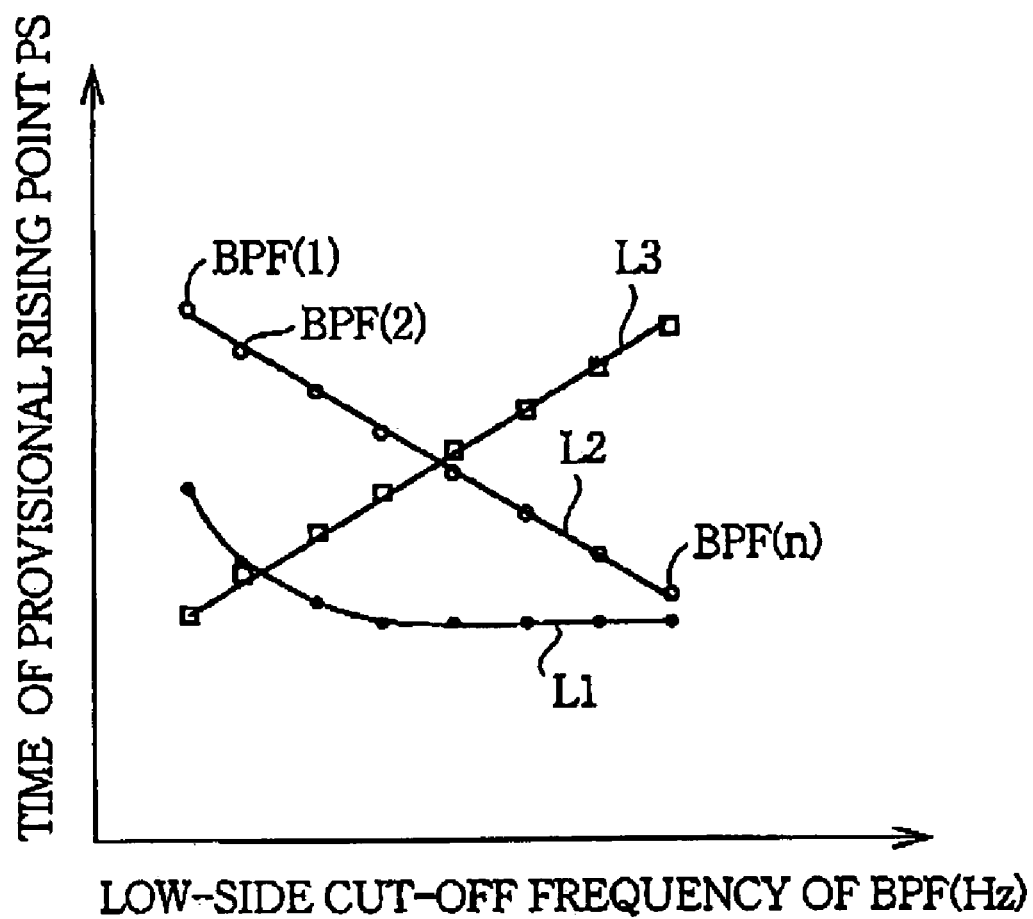
FIG. 6 is a graph showing respective times of a plurality of provisional rising points that are determined by a provisional rising point determining means, shown in FIG. 4, with respect to low-side cut-off frequency band of band-pass filter BPF.
Figure 7:
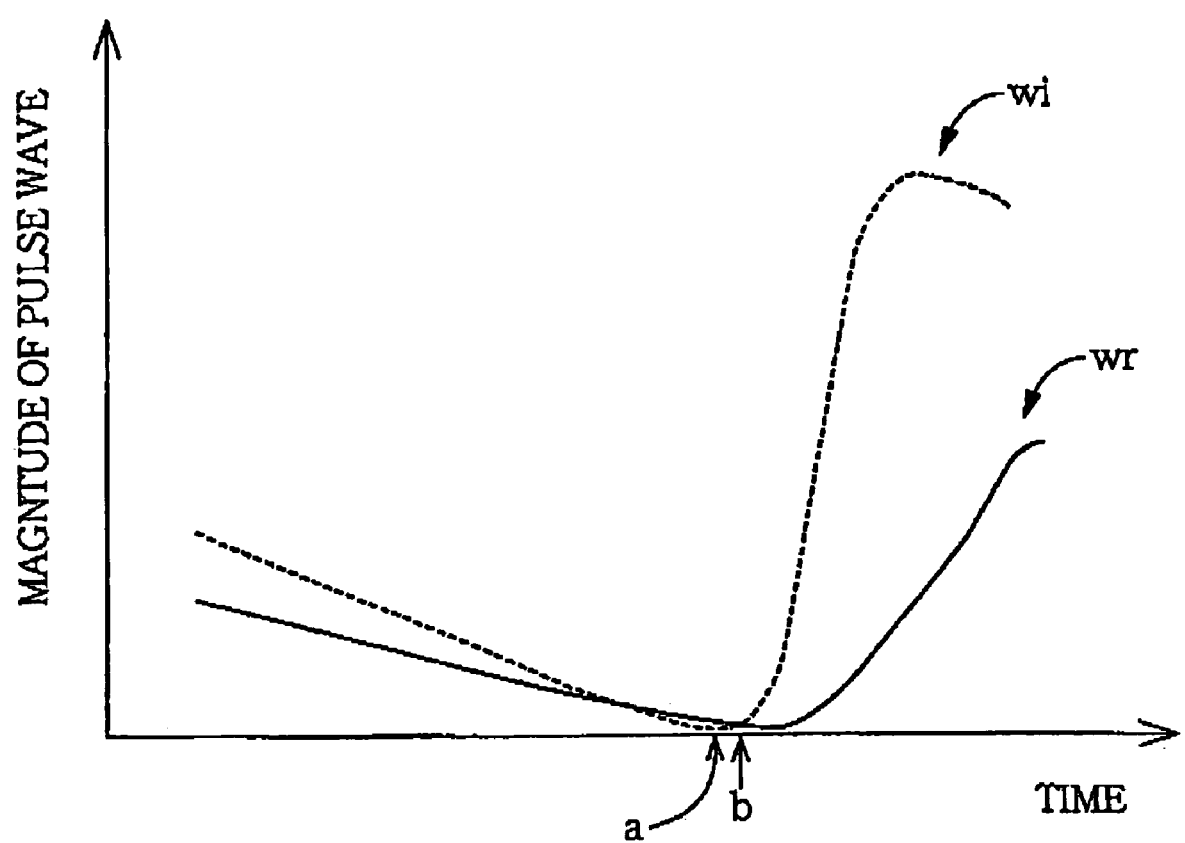
FIG. 7 is a view showing respective rising portions of an incident wave component, wi, and a reflected wave component, wr.

In a third case where the respective times PS of respective provisional rising points monotonously increase as the respective upper limits of respective low-side cut-off frequency bands of the band-pass filters 62 increase, as indicated at curve L3 in FIG. 6, the proper rising point determining means 66 selects, as the time AS of proper rising point, the shortest one of the respective times PS of respective provisional rising points, e.g., the time PS(1) shown in FIG. 6, because an amount of delay of the phase of high-frequency component of the pulse wave that occurs when the pulse wave as the pressure oscillation produced from the artery and transmitted to the cuff 12 propagates via the piping 20 to the pressure sensor 16, is thought to be so large as to influence the determination of time of rising point of the pulse wave. The shortest time PS of provisional rising point, selected as the time AS of proper rising point, is determined based on the pulse wave whose high-frequency component is the least, i.e., the pulse wave represented by the pulse wave signal that has passed through the band-pass filter 62, e.g., the filter BPF(1) shown in FIG. 6, whose low-side cut-off frequency band is the lowest.

Meanwhile, there are other cases, not shown in FIG. 6, for example, a case where respective times PS of respective provisional rising points irregularly change, unlike any of the curve or lines L1, L2, L3 shown in FIG. 6, as respective upper limits of respective low-side cutoff frequency bands increase or decrease; and a case where one or more (but not all of respective times PS of respective provisional rising points is or are excessively shorter or longer than the other times PS. Since, in those cases, disturbing noise is thought to have been mixed, the determining means 66 does not determine a time AS of a proper rising point, and operates the display device 48 to indicate that an error has occurred to measurement.

A pulse-wave propagation velocity determining device or means 68 first determines a time of detection of a start point of a heart sound I of the heart sound waveform represented by the heart sound signal SH supplied from the heart-sound microphone 34, in a state in which the cuff pressure changing means 50 maintains the cuff pressure PC at the prescribed pulse-wave detection pressure value, and additionally determines a time difference (sec) between the time of start point of the heart sound I and the time AS of proper rising point determined by the proper rising point determining means 66. i.e., a pulse-wave propagation time DT in which a pulse wave (i.e., the cuff pulse wave) propagates from the subjects heart to a portion of the subject (i.e., the brachium 14) where the cuff 12 is worn. The start point of heart sound I corresponds to the rising point of pulse wave. Then, the determining means 68 substitutes the subjects stature T represented by the stature signal ST supplied from the input device 40, with the above-indicated Expression 1. Thus, the determining means 68 determines the propagation distance L between the heart and the brachium 14. In addition, the determining means 68 substitutes the propagation distance L and the pulse-wave propagation time DT with the above-indicated Expression 2, so as to calculate a pulse-wave propagation velocity PWV (cm/sec). Finally, the determining means 68 operates the display device 48 to display the thus calculated pulse-wave propagation velocity PWV.

Figure 8:
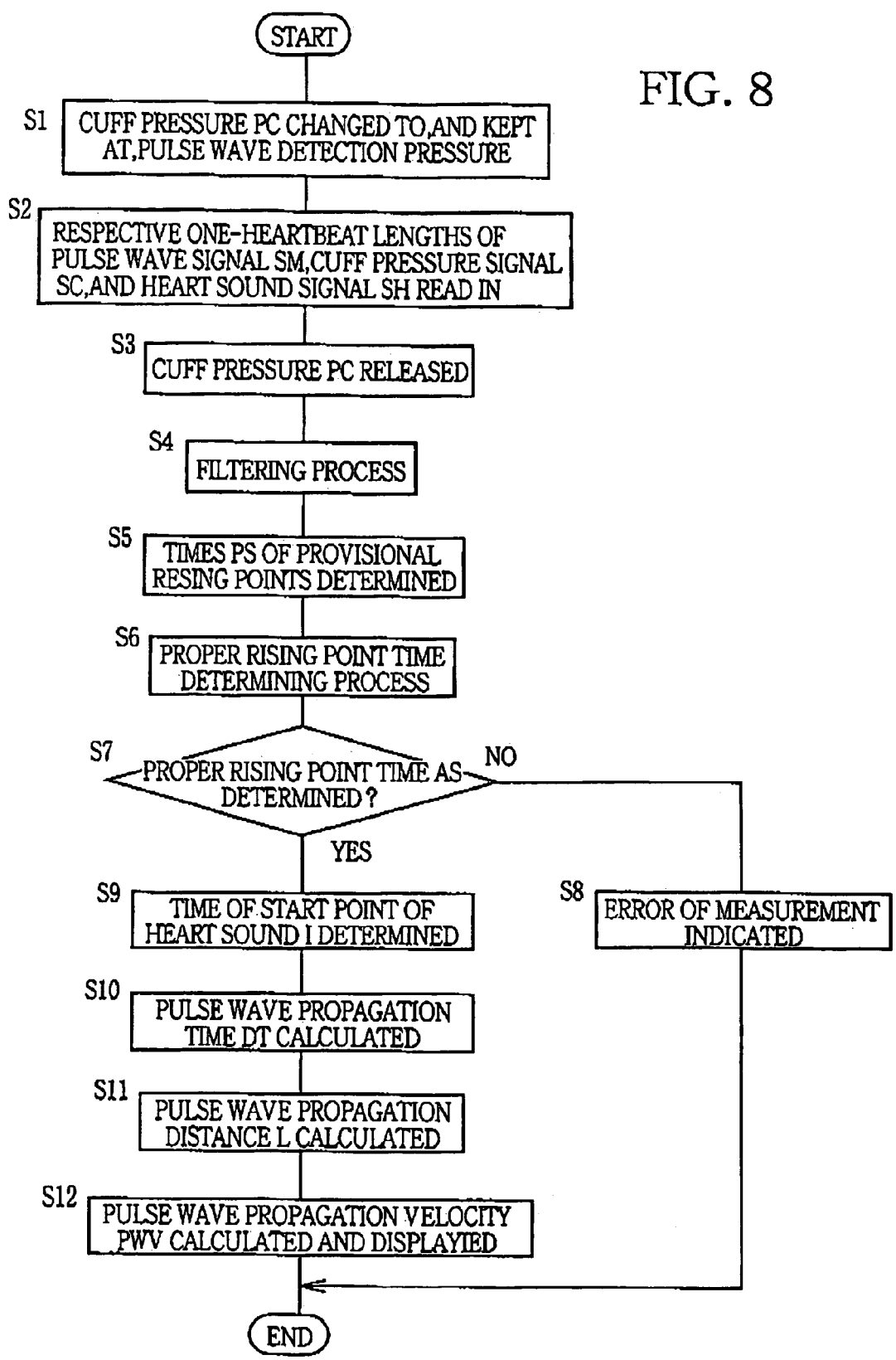
FIG. 8 is a flow chart representing essential control functions of a CPU (central processing unit), shown in FIG. 4.

FIG. 8 is a flow chart for explaining the essential control functions of the CPU 42, shown in FIG. 4. This flow chart is started upon operation of a start button, not shown, on the assumption that the stature signal ST has already been supplied from the input device 40 to the control device 30.

In FIG. 8, first, at Step S1, the CPU 42 starts the air pump 24 and operates the pressure control valve 18 to change and maintain the cuff pressure PC to and at the prescribed pulse wave detection pressure value, e.g., 50 mmHg.

Subsequently, at Step S2, in a state in which the cuff pressure PC is maintained at the pulse wave detection pressure value, the CPU 42 reads in respective lengths of the pulse wave signal SM, supplied from the pressure sensor 16, the cuff pressure signal SC, supplied from the static-pressure filter circuit 26, and the heart sound signal SH, supplied from the heart sound microphone 34 via the heart sound signal amplifier 36, all of which correspond to one heartbeat of the subject. Then, the control of the CPU 42 proceeds with Step S3 to operate the pressure control valve 18 to decrease the cuff pressure PC down to atmospheric pressure. In the embodiment shown in FIG. 8, Steps S1 and S3 correspond to the cuff pressure changing means 50.

Next, at Step S4, the CPU 42 filters the pulse wave signal SM, read in at Step S2, through each of the plurality of band-pass filters 62 (BPF(1), BPF(2), BPF(3), . . . , BPF(n)) as one of signal processing algorithms pre-stored in the ROM 44, and thereby obtains respective secondary pulse wave signals SM2(1), SM2(2), SM2(3), . . . , SM2(n). Subsequently, the control goes to Step S5 corresponding to the provisional rising point determining means 64. At Step S5, the CPU 42 determines respective times of detection of respective minimum points of respective heartbeat-synchronous pulses of respective pulse waves represented by the secondary pulse wave signals SM2(1), SM2(2), . . . , SM2(n), obtained at Step S4, as respective times PS(1), PS(2), . . . , PS(n) of detection of respective provisional rising points of the respective heartbeat-synchronous pulses of the respective pulse waves, Then, the control goes to Steps S6, S7, and S8 corresponding to the proper rising point determining means 66. First, at Step S6, the CPU 42 determines a time AS of detection of a proper rising point. More specifically described, in the first case where the respective times PS of detection of respective provisional rising points decrease as the respective upper limits of respective low-side cut-off frequency bands of the band-pass filters 62 increase, and simultaneously at least two times of the respective times PS are substantially equal to each other, for example, two or more times PS are substantially equal to each other in a relatively high frequency range, as indicated at curve L1 shown in FIG. 6, the CPU 42 determines the two or more times PS substantially equal to each other, as the time AS of detection of the proper rising point. In the second or third case where the respective times PS of detection of respective provisional rising points decrease, or increase, as the respective upper limits of respective low-side cut-off frequency bands of the band-pass filters 62 increase, as indicated at line L2 or Line L3 shown in FIG. 6, the CPU 42 determines the shortest time of the respective times PS as the time AS of detection of the proper rising point. In other cases, for example, in the case where the respective times PS of respective provisional rising points irregularly change, unlike any of the curve or lines L1, L2, L3 shown in FIG. 6, as the respective upper limits of respective low-side cut-off frequency bands increase or decrease, or in the case where one or more (but not all) of the respective times PS of respective provisional rising points is or are excessively shorter or longer than the other times PS, the CPU 42 does not determine the time AS of proper rising point.

Subsequently, at Step S7, the CPU 42 judges whether the time AS of proper rising point has been determined at Step S6. If a positive judgment is made at Step S7, then the control goes to Step S9. On the other hand, if a negative judgment is made, the control goes to Step S8 to operate the display device 48 to indicate that an error has occurred to the measurement of the time AS of proper rising point.

Steps S9, S10, and S11 correspond to the pulse-wave propagation velocity determining means 68. First, at Step S9, the CPU 42 determines a time of detection of a start point of a heart sound I of the heart-sound waveform represented by the heart sound signal SH, read in at Step S2. Subsequently, at Step S10, the CPU 42 calculates a time difference between the time of detection of the start point of heart sound I, determined at Step S9, and the time AS of proper rising point, determined at Step S6, that is, a pulse wave propagation time DT.

Then, at Step S11, the CPU 42 substitutes the subject's stature T represented by the stature signal ST supplied in advance from the input device 40, with the above-indicated Expression 1, so as to calculate a pulse wave propagation distance L. Next, at Step S12, the CPU 42 substitutes the propagation distance L, calculated at Step S11, and the pulse wave propagation time DT, calculated at Step S10, with the above-indicated Expression 2, so as to calculate a pulse wave propagation velocity PWV. Finally, the CPU 42 operates the display device 48 to display the thus calculated pulse-wave propagation velocity PWV. Thus, this routine is finished.

In the illustrated embodiment, the provisional rising point determining device or means 64 (Step S5) determining the respective times PS(1), PS(2), . . . PS(n) of respective provisional rising points of respective pulse waves represented by the respective secondary pulse wave signals SM2(1), SM2(2), . . . , SM2(n) that have passed through the band-pass filters 62 having respective different low-side cut-off frequency bands, and the proper rising point determining device or means 66 (Steps S6, S7, and S8) compares the respective times PS of respective provisional rising points with each other and thereby determines the time AS of proper rising point based on the respective times PS of respective provisional rising points. Therefore, even if respective rising portions of respective reflected wave components and/or respective incident wave components of respective pulse waves detected from different patients may have different frequencies or different frequency bands, the present pulse-wave propagation velocity measuring apparatus (the pulse-wave analyzing apparatus) 60 can accurately determine a rising point of a pulse wave detected from each of the patients.

While the present invention has been described in detail in its preferred embodiment by reference to the drawings, it is to be understood that the invention may otherwise be embodied.

For example, in the above-described embodiments, the band-pass filter 28, or each of the band-pass filters 62 is employed as the pulse wave filter for use with the pulse wave sensor, i.e., the cuff 12. However, the band-pass filter 28, or each of the band-pass filters 62 may be replaced with a high-pass filter.

In addition, in each of the above-described embodiments, the cuff 12 as the pulse wave sensor is worn on the brachium 14 of the subject. However the body portion of a subject on which the pulse wave sensor is worn is not limited to the brachium 14 of the subject, but may be any portion from which a pulse wave can be detected, for example, wrist, the tip of a finger, femoral portion, or ankle. However, since respective pulse waves detected from different body portions of a subject have different frequencies, the pulse wave filter for use with the pulse wave sensor is adapted to have an appropriate one or ones of different low-side cut-off frequency bands and/or different specific frequency bands corresponding to different body portions of a subject where the pulse wave sensor is worn. For example, in the case where a cuff as a pulse wave sensor is worn on an ankle of a subject, a pulse wave filter for use with the cuff is adapted to have a specific frequency band of from 1 Hz to 15 Hz.

In the second embodiment shown in FIGS. 3 to 8, the digital filters (band-pass filters) 62 are employed as the pulse wave filters for use with the cuff 12 as the pulse wave sensor. However, the digital filters 62 may be replaced with analog filters each of which is provided by an electronic circuit or circuits.

In addition, in each of the above-described embodiments, the minimum-point detecting method is employed as the method of identifying or determining the time of detection of the rising point or the provisional rising point. However, the rising point may be determined by well-known other rising-point determining methods, such as second-order differentiation method or tangential line method.

In addition, in each of the above-described embodiments, the upstream-side and downstream-side ends of the measurement interval in which pulse-wave propagation velocity PWV is measured is the heart and the brachium 14 of the subject, respectively. However, a different measurement interval may be employed to measure pulse-wave propagation velocity PWV. For example, in the case where another cuff as another pulse wave sensor is worn on an ankle of the subject, a pulse-wave propagation velocity PWV may be measured by using first measurement interval between the heart and the brachium 14 of the subject, and a second measurement interval between the heart and the ankle of the subject It is to be understood that the present invention may be embodied with other changes, improvements and modifications that may occur to a person skilled in the art without departing from the spirit and scope of the invention defined in the appended claims.

What is claimed is:

1. A pulse wave analyzing apparatus, comprising:
   a pulse wave sensor which is adapted to be worn on a body portion of a living subject to detect a pulse wave from the body portion, and outputs a pulse wave signal representing the detected pulse wave;
   a plurality of filters for use with the pulse wave sensor, the plurality of filters having respective low-side cut-off frequency bands differing from each other, and each receiving the pulse wave signal outputted by the pulse wave sensor;

a provisional rising point determining means for determining a time of detection of a provisional rising point of each of respective pulse waves represented by respective signals that have passed through the filters; and a proper rising point determining means for comparing the respective times of detection of the respective provisional rising points, each determined by the provisional rising point determining means, with each other, and thereby determining a time of detection of a proper rising point based on the respective times of detection of the respective provisional rising points.

2. The pulse wave analyzing apparatus according to claim 1, wherein the proper rising point determining means determines, when at least two times of the respective times of detection of the respective provisional rising points are substantially equal to each other, said at least two times substantially equal to each other, as the time of detection of the proper rising point.

3. The pulse wave analyzing apparatus according to claim 1, wherein the proper rising point determining means determines, when the respective times of detection of the respective provisional rising points of the respective pulse waves represented by the respective signals that have passed through the filters decrease as respective upper limits of the respective low-side cut-off frequency bands of the corresponding filters increase, a shortest one of the respective times of detection of the respective provisional rising points, as the time of detection of the proper rising point.

4. The pulse wave analyzing apparatus according to claim 1, wherein the pulse-wave sensor comprising an inflatable cuff adapted to be worn on the body portion of the subject, and wherein the proper rising point determining means determines, when the respective times of detection of the respective provisional rising points of the respective pulse waves represented by the respective signals that have passed through the filters increase as respective upper limits of the respective low-side cut-off frequency bands of the corresponding filters increase, a shortest one of the respective times of detection of the respective provisional rising points, as the time of detection of the proper rising point.

5. A pulse wave analyzing apparatus, comprising:

a pulse wave sensor which is adapted to be worn on a body portion of a living subject to detect a pulse wave from the body portion, and outputs a pulse wave signal representing the detected pulse wave;

a plurality of filters for use with the pulse wave sensor, the plurality of filters having respective low-side cut-off frequency bands differing from each other, and each receiving the pulse wave signal outputted by the pulse wave sensor;

a provisional rising point determining device which determines a time of detection of a provisional rising point of each of respective pulse waves represented by respective signals that have passed through the filters; and a proper rising point determining device which compares the respective times of detection of the respective provisional rising points, each determined by the provisional rising point determining device, with each other, and thereby determining a time of detection of a proper rising point based on the respective times of detection of the respective provisional rising points.

* * * * *